(12) United States Patent
Ou et al.

(10) Patent No.: US 9,309,169 B2
(45) Date of Patent: Apr. 12, 2016

(54) PROCESS FOR THE PRODUCTION OF PURIFIED XYLENE ISOMERS

(71) Applicant: ExxonMobil Chemical Patents Inc., Baytown, TX (US)

(72) Inventors: John Di-Yi Ou, Houston, TX (US); Ronald L. DeMartino, Kingwood, TX (US); Jeevan S. Abichandani, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 162 days.

(21) Appl. No.: 14/080,963

(22) Filed: Nov. 15, 2013

(65) Prior Publication Data

US 2014/0155667 A1 Jun. 5, 2014

Related U.S. Application Data

(60) Provisional application No. 61/732,139, filed on Nov. 30, 2012.

(51) Int. Cl.
| | |
|---|---|
| *C07C 5/27* | (2006.01) |
| *C07C 4/18* | (2006.01) |
| *C07C 7/04* | (2006.01) |
| *C07C 7/12* | (2006.01) |
| *C07C 7/14* | (2006.01) |

(52) U.S. Cl.
CPC ............... *C07C 4/18* (2013.01); *C07C 5/2702* (2013.01); *C07C 5/2737* (2013.01); *C07C 7/04* (2013.01); *C07C 7/12* (2013.01); *C07C 7/14* (2013.01); *C07C 2529/70* (2013.01)

(58) Field of Classification Search
USPC .................................................. 585/478, 477
See application file for complete search history.

(56) References Cited

U.S. PATENT DOCUMENTS

| | | |
|---|---|---|
| 3,856,874 A | 12/1974 | Hayward |
| 6,180,550 B1 | 1/2001 | Beck et al. |
| 6,198,013 B1 | 3/2001 | Mohr et al. |
| 6,448,459 B1 | 9/2002 | Magne-Drisch et al. |
| 6,689,929 B2 | 2/2004 | Williams et al. |
| 6,872,866 B1 | 3/2005 | Nemeth et al. |
| 6,878,855 B2 | 4/2005 | Deckman et al. |
| 7,179,367 B2 | 2/2007 | Feng et al. |
| 7,244,409 B2 | 7/2007 | Burgfels et al. |
| 7,368,620 B2 | 5/2008 | Zhou et al. |
| 7,371,913 B2 | 5/2008 | Bauer |
| 7,439,412 B2 | 10/2008 | Ou et al. |

(Continued)

FOREIGN PATENT DOCUMENTS

| | | |
|---|---|---|
| WO | WO 00/10944 | 3/2000 |
| WO | 2005-075389 | 8/2005 |

(Continued)

OTHER PUBLICATIONS

U.S. Appl. No. 60/794,864, filed Apr. 25, 2006, Ou, et al.

(Continued)

*Primary Examiner* — Thuan D Dang (57) ABSTRACT

The invention is directed to a process to produce para-xylene and optionally, ortho-xylene, including coupling a $C_9^+$-aromatics-removal system with an isomerization system or with a parallel configuration of two isomerization systems to reduce xylenes recycle for energy savings and/or productivity increases.

21 Claims, 3 Drawing Sheets

Improved PX Production Process

(56) References Cited

U.S. PATENT DOCUMENTS

| | | |
|---|---|---|
| 7,495,137 B2 | 2/2009 | Zhou et al. |
| 7,553,998 B2 | 6/2009 | Bresler et al. |
| 7,592,499 B2 | 9/2009 | Wolff et al. |
| 7,626,065 B2 | 12/2009 | Ou et al. |
| 7,663,010 B2 | 2/2010 | Levin |
| 7,683,233 B2 | 3/2010 | Ou et al. |
| 7,989,672 B2 | 8/2011 | Kinn et al. |
| 2007/0249882 A1 | 10/2007 | Ou et al. |
| 2008/0262282 A1 | 10/2008 | Leflaive et al. |
| 2009/0149686 A1 | 6/2009 | Leflaive et al. |
| 2009/0182182 A1 | 7/2009 | Bauer |
| 2010/0152508 A1 | 6/2010 | Ou et al. |
| 2011/0092755 A1 | 4/2011 | Lattner et al. |
| 2011/0319688 A1 | 12/2011 | Ou |
| 2012/0108868 A1 | 5/2012 | Pilliod et al. |
| 2012/0330075 A1 | 12/2012 | Ou et al. |

FOREIGN PATENT DOCUMENTS

| | | |
|---|---|---|
| WO | 2005-075390 | 8/2005 |
| WO | WO 2007/127049 | 11/2007 |
| WO | 2011-133326 | 10/2011 |
| WO | 2012-058106 | 5/2012 |
| WO | 2012-058108 | 5/2012 |

OTHER PUBLICATIONS

U.S. Appl. No. 60/844,430, filed Sep. 14, 2006, Ou, et al.

U.S. Appl. No. 61/326,445, Apr. 21, 2010, Ou et al.

Figure 1
Conventional PX Production Process

Figure 2
Improved PX Production Process

Figure 3
Improved PX Production Process

PROCESS FOR THE PRODUCTION OF PURIFIED XYLENE ISOMERS

CROSS-REFERENCE OF RELATED APPLICATIONS

This application claims priority to and the benefit of Provisional Application No. 61/732,139, filed Nov. 30, 2012.

FIELD OF THE INVENTION

The invention relates generally to the production of xylenes, including separation of $C_8$ aromatics and reactions of $C_8$ aromatics including xylenes isomerization, ethylbenzene de-ethylation, and/or isomerization; and also to an apparatus for the practice of said process.

BACKGROUND OF THE INVENTION

Xylene isomers are important intermediates, which find wide and varied applications in chemical syntheses. By way of example, para-xylene (PX) is a feedstock for terephthalic acid which finds use in the manufacture of synthetic fibers; meta-xylene (MX) is used in the manufacture of dyes; and ortho-xylene (OX) is used as a feedstock for phthalic anhydride which finds use in the manufacture of plasticizers.

$C_8$ aromatics, such as xylenes are found in various fractions from the petrochemical industry, such as coal tar distillate, petroleum reformates, and pyrolysis liquids in admixture with other compounds of like boiling points. The aromatic components from these materials, such $C_8$ aromatics or even xylenes, are readily separated from non-aromatics by methods such as solvent extraction or distillation.

While difficult to separate due to their similar chemical structures and physical properties and identical molecular weights, there are various methods used for separating $C_8$ isomers, for instance OX is separable from other $C_8$ aromatics by fractional distillation, and PX is separable by fractional crystallization or selective adsorption.

The production of PX in a conventional aromatics complex is energy intensive. This is due in a significant part to the equilibrium limitation on PX concentration imposed by the thermodynamics. Under the typical conditions of 200° C. to 500° C. at which xylenes are processed in a typical petrochemical plant, the thermodynamic equilibrium content calculated based on free energy of formation is often approximately 24 mol % PX, 56 mol % MX, and 20 mol % OX, based on the total amount of xylenes in the feed. Such a relatively low PX equilibrium concentration leads to large amounts of MX and OX recycles which are reprocessed through several energy intensive operations, making PX production a costly practice in terms of energy consumption and capital investments. Present demand for PX is fairly large and is expected to grow in the future. Consequently, a system maximizing PX production in an energy-efficient manner is highly sought after.

Figure 1:
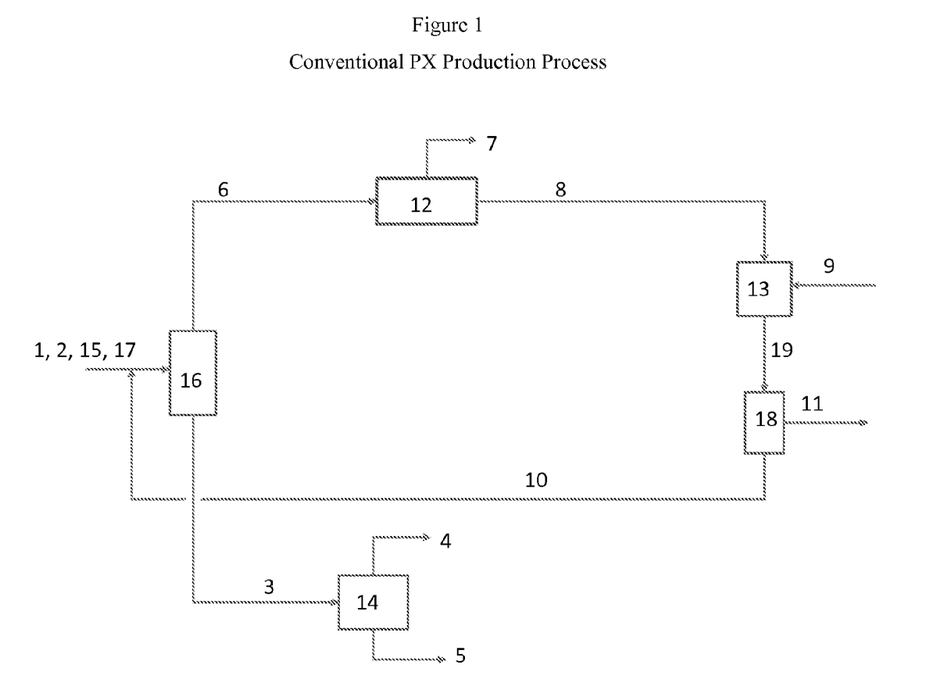
FIG. 1 is a schematic illustrating typical processing of $C_8^+$ aromatics to produce PX and optionally OX.

A typical process is illustrated in FIG. 1. The feed streams to the system comprise $C_8^+$ aromatics and may come from one or more sources, including $C_8^+$ reformate 1 (see, for instance, U.S. Pat. No. 7,179,367), $C_8^+$ selective toluene disproportionation product 17 (see, for instance, U.S. Pat. No. 7,989,672), $C_8^+$ transalkylation product 2 (see, for instance, U.S. Pat. No. 7,663,010), $C_8^+$ toluene disproportionation product 15 (see, for instance, U.S. Pat. No. 6,198,013), and $C_8$ aromatics, produced from toluene and/or benzene methylation with methanol (see, for instance, U.S. Application 2011/0092755). These streams typically comprise $C_8$ and heavier aromatics which are processed along with a recycle stream 10 in one or more fractionators 16 for the removal $C_9^+$-aromatics (aromatic compounds having nine or more carbon atoms) and, optionally, OX in stream 3, which optionally can be subsequently separated in fractionator 14 into OX overhead 4 and $C_9^+$ bottoms 5. The $C_9^+$-aromatics could have adverse effects on downstream PX Recovery 12 and vapor-phase xylenes isomerization unit 13 if not removed from the feed stream(s) as bottoms by the aforementioned fractionation unit 16 and, optionally, 14.

The removal of $C_9^+$-aromatics and, optionally, OX in fractionator(s) 16 thus yields an overhead of $C_8$-aromatics-rich stream 6 which typically contains PX at a concentration of below or near the thermodynamic equilibrium concentration. The $C_8$-aromatics-rich stream 6 is processed to selectively recover PX by one or both of selective adsorption or crystallization which is shown as PX recovery 12. The PX product stream 7 typically having more than 99.7 wt % PX is recovered, and the balance of $C_8$ aromatics stream 8 passes to vapor-phase xylenes isomerization 13. Usually, in the presence of hydrogen in stream 9, vapor-phase xylenes isomerization 13 generates an isomerate (i.e., isomerization product) stream 19 having near-equilibrium concentration of xylene isomers using one or more of a variety of catalysts which may also convert EB to benzene and ethane or may convert EB to near-equilibrium xylene isomers. The isomerate, or isomerization product stream 19, passes to detoluenization fractionation 18 which removes $C_7$-hydrocarbons (hydrocarbon compounds having seven or less carbon atoms) in stream 11 to yield isomerate recycle stream 10. Isomerate recycle stream 10 is processed in the fractionator 16.

Improving such an energy-intensive process is an active area of research, but it is not a simple matter of optimization of each individual step, as optimization of one step may negatively affect one or more steps in the overall system. Examples of proposed improvements include the following.

U.S. Pat. No. 3,856,874 describes splitting the effluent stream from PX recovery, passing the independent streams over different catalysts, then combining the isomerized streams and recycling.

U.S. Pat. No. 7,439,412 discloses a process for recovering one or more high purity xylene isomers from a $C_8^+$-aromatic feed stream including the use of an isomerization unit under liquid-phase conditions. In an example, the product of the liquid-phase isomerization unit is returned to the first fractionation tower in the system. See also U.S. Pat. No. 7,626,065.

U.S. Pat. No. 7,553,998 discloses a process for recovering one or more high-purity xylene isomers from a feed having substantial content of $C_9^+$-aromatic hydrocarbons comprising de-ethylation of heavy aromatics followed by fractionation and then passing the stream to a $C_8$-aromatic-isomer recovery to recover high-purity xylene isomers with lowered energy costs. Streams passing through an isomerization unit under liquid isomerization conditions are split, with a portion sent to an isomer recovery unit, and a portion is purged.

WO 2012/058106 and WO 2012/058108 describe processes for producing a PX-rich product, such as (a) providing a PX-depleted stream; (b) providing a parallel configuration of vapor-phase and liquid-phase isomerization units; and (c) splitting the PX-depleted stream and isomerizing the two split streams in the two parallel isomerization units respectively. The process saves energy by reducing the amounts of isomerate recycle from vapor-phase xylenes isomerization which is more energy intensive than liquid-phase xylenes isomerization.

WO 2011/133326 is directed to a xylenes isomerization process, including a liquid-phase isomerization, for the production of equilibrium or near-equilibrium xylenes, wherein the process conditions include a temperature of less than 295° C. and a pressure sufficient to maintain the xylenes in liquid phase that uses at most only ppm levels of hydrogen and that in embodiments can be regenerated numerous times by an in situ procedure.

Other references of interest include U.S. Patent Application Publication Nos. 2008/0262282; 2009/0149686; 2009/0182182; U.S. Pat. Nos. 6,448,459; 6,872,866; and 7,368,620.

Present demand for PX is fairly large and is expected to grow in the future. Consequently, a system maximizing PX production in an energy-efficient manner is highly sought after. While prior attempts to improve PX and optionally OX production abound, most have not been able to overcome the xylenes equilibrium limitation to reduce xylenes recycle. The present inventors have surprisingly discovered a process which overcomes the equilibrium limitation to reduce xylenes recycle by coupling a $C_9^+$-aromatics-removal system with an isomerization system or coupling a $C_9^+$-aromatics-removal system with a parallel configuration of two isomerization systems. The improved process significantly reduces the energy required and/or increases the production capacity for producing high purity PX and optionally OX.

SUMMARY OF THE INVENTION

The invention is directed to a process for producing PX comprising (1) supplying a hydrocarbon feed comprising $C_8^+$ aromatics (preferably PX and at least one of MX, OX, and EB) to a PX production system (also called a PX production loop) comprising a $C_9^+$-aromatics-removal system, a PX-recovery system, a first isomerization system, a second isomerization system, and a $C_7^-$ hydrocarbons-removal system; (2) separating $C_9^+$ aromatics from said feed in said $C_9^+$-aromatics-removal system to recover: a) at least one $C_8$-aromatics stream, b) at least one PX-lean stream having a lower PX concentration than said $C_8$-aromatics stream(s), and c) at least one $C_9^+$-aromatics-rich stream; (3) separating said $C_8$-aromatics stream in said PX-recovery system to recover a PX-rich stream and a PX-depleted stream; (4) isomerizing at least partially in the vapor phase said PX-depleted stream in said first isomerization system to produce a first isomerized stream having a higher PX concentration than said PX-depleted stream; (5) separating $C_7^-$ hydrocarbons from said first isomerized stream in said $C_7^-$ hydrocarbons-removal system to produce a $C_7^-$ hydrocarbons-rich stream and a $C_7^-$ hydrocarbons-depleted isomerized stream having a lower $C_7^-$ hydrocarbons concentration than said first isomerized stream; (6) recycling said $C_7^-$ hydrocarbons-depleted isomerized stream to said $C_9^+$-aromatics-removal system; (7) isomerizing at least partially in the liquid phase said PX-lean stream in said second isomerization system to produce a second isomerized stream having a higher PX concentration than said PX-lean stream; and (8) recycling said second isomerized stream to said $C_9^+$-aromatics-removal system. Optionally, the $C_9^+$-aromatics-rich stream may then be separated downstream of step (2), such as by fractionation, to produce an OX-rich steam and an OX-depleted $C_9^+$ stream.

This invention also relates to an apparatus for the production of PX and, optionally, OX comprising a first fractionation column operating at conditions suitable for the separation of $C_8^+$ aromatics streams into a $C_8$-aromatics overhead stream, a PX-lean middle stream having a lower PX concentration than said $C_8$-aromatics overhead stream, and a $C_9^+$-aromatics-rich bottom stream, said $C_8$-aromatics overhead stream is fluidly connected with a PX-recovery unit, wherein said PX-recovery unit provides a PX-rich stream and a PX-depleted stream, said PX-depleted stream is fluidly connected with a vapor-phase isomerization unit to produce a first isomerized stream which is fluidly connected with a second fractionation column operating at conditions suitable for separating said first isomerized stream into a $C_7^-$ hydrocarbons-rich overhead stream and a $C_7^-$ hydrocarbons-depleted bottom stream, said $C_7^-$ hydrocarbons-depleted bottom stream is fluidly connected with said first fractionation column to effect a recycle, the improvement comprising connecting fluidly said PX-lean middle stream with a liquid-phase isomerization unit to produce a second isomerized stream which is connected fluidly with said first fractionation column to effect another recycle.

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION

For the purposes of this invention and the claims thereto, "$C_8$ aromatics" shall mean aromatic compounds having eight carbon atoms, including ethylbenzene (EB), para-xylene (PX), meta-xylene (MX), and ortho-xylene (OX); "$C_8^+$ aromatics" shall mean aromatic compounds having eight or more carbon atoms, including ethylbenzene (EB), para-xylene (PX), meta-xylene (MX), and ortho-xylene (OX); $C_9^+$-aromatics shall mean aromatic compounds having nine or more carbon atoms; $C_7^-$ hydrocarbons shall mean hydrocarbons having seven carbon atoms or less; "lean" shall mean less than the equilibrium concentration at the same process conditions, for example, a PX-lean stream is one where the PX concentration based on the total amount of xylenes in the stream is less than the equilibrium concentration at the same process conditions; "rich" shall mean higher than the starting concentration, for example, a PX-rich stream derived from a starting stream is one where the PX concentration based on the total amount of xylenes in the stream is higher than the PX concentration in the starting stream; and "depleted" shall mean lower than the starting concentration, for example, a PX-depleted stream derived from a starting stream is one where the PX concentration based on the total amount of xylenes in the stream is lower than the PX concentration in the starting stream.

The phrase "near-equilibrium concentration of xylene isomers" shall mean the concentration of PX based on the total amount of xylenes in the stream is within 85% to 100% of its equilibrium concentration while the concentrations of MX and OX vary to balance the composition. For example, if the xylene equilibrium concentrations are 24 wt % PX, 56 wt % MX, and 20 wt % OX at 350° C., then a stream having the xylene concentrations of 21 wt % PX, 58 wt % MX, and 21 wt % OX at 350° C. would be having a near-equilibrium concentration of xylene isomers.

The phrase "away from equilibrium" shall mean the concentration of PX based on the total amount of xylenes in the stream is below 85% of its equilibrium concentration while the concentrations of MX and OX vary to balance the composition. For example, if the xylene equilibrium concentrations are 24 wt % PX, 56 wt % MX, and 20 wt % OX at 350° C., then a stream having the xylene concentrations of 18 wt % PX, 60 wt % MX, and 22 wt % OX at 350° C. would be away from equilibrium.

The phrase "near thermodynamic equilibrium" shall have the same meaning as near-equilibrium concentration of xylene isomers.

The invention is related to an unexpected discovery that in the separation of $C_9^+$-aromatics from a $C_8^+$ aromatics feedstock, there exist PX-lean streams in addition to the two commonly known products of a $C_8$-aromatics stream and a $C_9^+$-aromatics-rich stream, e.g., the overhead product and the bottom product of a xylene rerun distillation column, respectively. The invention is further related to another unexpected discovery that the xylenes (ortho, meta, and para) concentrations in said PX-lean streams are away from equilibrium. The invention is further related to yet another unexpected discovery that isomerizing the $C_8$ aromatics in said PX-lean streams to near thermodynamic equilibrium raises the PX concentration in said $C_8$-aromatics stream to above the PX equilibrium concentration at temperatures typical to PX production, such as from 200° C. to 500° C.

According to the invention, a system is provided which (1) generates at least one PX-lean stream in the separation of $C_9^+$-aromatics from $C_8^+$ aromatics feedstocks; (2) isomerizes the $C_8$ aromatics in said PX-lean stream(s) in either a liquid-phase isomerization unit or a parallel configuration of a liquid-phase and a vapor-phase isomerization units to generate an isomerate (product of isomerization); and (3) recycles said isomerate to said $C_9^+$-aromatics separation. Due to the coupling of $C_9^+$-aromatics separation and $C_8$ aromatics isomerization, such a system is capable of increasing the PX concentration in said $C_8$ aromatics product stream to above the thermodynamic equilibrium concentration, which significantly reduces the quantity of xylenes recycle and the energy required for recycle processing. The benefits of such improvements may be realized in several ways including saving energy at constant PX production, maximizing capacity to increase PX production, or both.

The invention is directed to a process for producing PX comprising (1) supplying a hydrocarbon feed comprising PX and at least one of MX, OX and EB (typically comprising PX, MX, OX and EB) to a PX production loop comprising a $C_9^+$-aromatics-removal system, a PX-recovery system, a first isomerization system, a second isomerization system, and a $C_7^-$ hydrocarbons-removal system; (2) separating $C_9^+$-aromatics from said feed in said $C_9^+$-aromatics-removal system to recover: a) at least one $C_8$-aromatics stream, b) at least one PX-lean stream having a lower PX concentration than said $C_8$-aromatics stream(s), and c) at least one $C_9^+$-aromatics-rich stream; (3) separating said $C_8$-aromatics stream in said PX-recovery system to recover a PX-rich stream and a PX-depleted stream; (4) isomerizing at least partially in the vapor phase said PX-depleted stream in said first isomerization system to produce a first isomerized stream having a higher PX concentration than said PX-depleted stream; (5) separating $C_7^-$ hydrocarbons from said first isomerized stream in said $C_7^-$ hydrocarbons-removal system to produce a $C_7^-$ hydrocarbons-rich stream and a $C_7^-$ hydrocarbons-depleted isomerized stream having a lower $C_7^-$ hydrocarbons concentration than said first isomerized stream; (6) recycling said $C_7^-$ hydrocarbons-depleted isomerized stream to said $C_9^+$-aromatics-removal system; (7) isomerizing at least partially in the liquid phase said PX-lean stream in said second isomerization system to produce a second isomerized stream having a higher PX concentration than said PX-lean stream; and (8) recycling said second isomerized stream to said $C_9^+$-aromatics-removal system. Optionally, the $C_9^+$-aromatics-rich stream may then be separated downstream of step (2), such as by fractionation, to produce an OX-rich steam and an OX-depleted $C_9^+$ stream.

In embodiments, said process comprises isomerizing at least partially in the liquid phase at least a portion of said PX-depleted stream in said second isomerization system to produce at least a portion of said second isomerized stream having a higher PX concentration than said PX-depleted stream.

In embodiments, said process comprises isomerizing at least partially in the vapor phase at least a portion of said PX-lean stream in said first isomerization system to produce at least a portion of said first isomerized stream having a higher PX concentration than said PX-lean stream.

In embodiments, said process comprises separating $C_7^-$ hydrocarbons from at least a portion of said second isomerized stream in said $C_7^-$ hydrocarbons-removal system to produce at least a portion of said $C_7^-$ hydrocarbons-depleted isomerized stream having a lower $C_7^-$ hydrocarbons concentration than said second isomerized stream.

In embodiments, said process comprises processing said second isomerized stream in a benzene removal system to produce a benzene-rich stream and a benzene-depleted stream, and recycling said benzene-depleted stream to said $C_9^+$-aromatics-removal system and/or said PX-recovery system.

In embodiments, said two parallel isomerization systems comprise a liquid-phase reaction system and a vapor-phase isomerization system, each of which comprises at least one of xylenes isomerization, EB dealkylation, and EB isomerization.

In embodiments, said $C_9^+$-aromatics-removal system and said $C_7^-$ hydrocarbons-removal system each comprises at least one distillation column.

The invention also relates to an apparatus for the production of PX and, optionally, OX comprising a first fractionation column operating at conditions suitable for the separation of $C_8^+$ aromatics streams into a $C_8$-aromatics overhead stream, a PX-lean middle stream having a lower PX concentration than said $C_8$-aromatics overhead stream, and a $C_9^+$-aromatics-rich bottom stream. Said $C_8$-aromatics overhead stream is fluidly connected with a PX-recovery unit, wherein said PX-recovery unit provides a PX-rich stream and a PX-depleted stream. Said PX-depleted stream is fluidly connected with a vapor-phase isomerization unit to produce a first isomerized stream, which is fluidly connected with a second fractionation column operating at conditions suitable for separating said first isomerized stream into a $C_7^-$ hydrocarbons-rich overhead stream and a $C_7^-$ hydrocarbons-depleted bottom stream. Said $C_7^-$ hydrocarbons-depleted bottom stream is fluidly connected with said first fractionation column to effect a recycle. One of the improvements comprises connecting fluidly said PX-lean middle stream with a liquid-phase isomerization unit to produce a second isomerized stream which is connected fluidly with said first fractionation column to effect another recycle.

Another improvement comprises connecting fluidly said PX-lean middle stream with said vapor-phase isomerization unit so that a portion of said PX-lean stream is passed to said vapor-phase isomerization unit and another portion of said PX-lean stream is passed to said liquid-phase isomerization unit.

Yet another improvement comprises connecting fluidly said PX-depleted stream with said liquid-phase isomerization unit so that a portion of said PX-depleted stream is passed to said liquid-phase isomerization unit and another portion of said PX-depleted stream is passed to said vapor-phase isomerization unit.

Yet another improvement comprises connecting fluidly said second isomerized stream to said second fractionation column so that at least a portion of said second isomerized stream is passed to said second fractionation column.

Yet another improvement comprises connecting fluidly said second isomerized stream with a third fractionation column to produce a benzene-rich overhead stream and a benzene-depleted bottom stream, and connecting fluidly said benzene-depleted bottom stream with said first fractionation column and/or said PX recovery-unit.

In embodiments, said vapor-phase and liquid-phase isomerization units are each selected from at least one of xylenes isomerization, EB dealkylation, and EB isomerization.

In embodiments, said PX recovery unit is selected from at least one of a crystallizer and an adsorptive separator.

It is an object of the invention to significantly reduce the energy required to produce PX and, optionally, OX by minimizing the amount of xylenes recycle.

It is yet another object of the invention to significantly increase the plant output for PX and, optionally, OX productions by utilizing the additional capacity created through recycle minimization.

Figure 2:
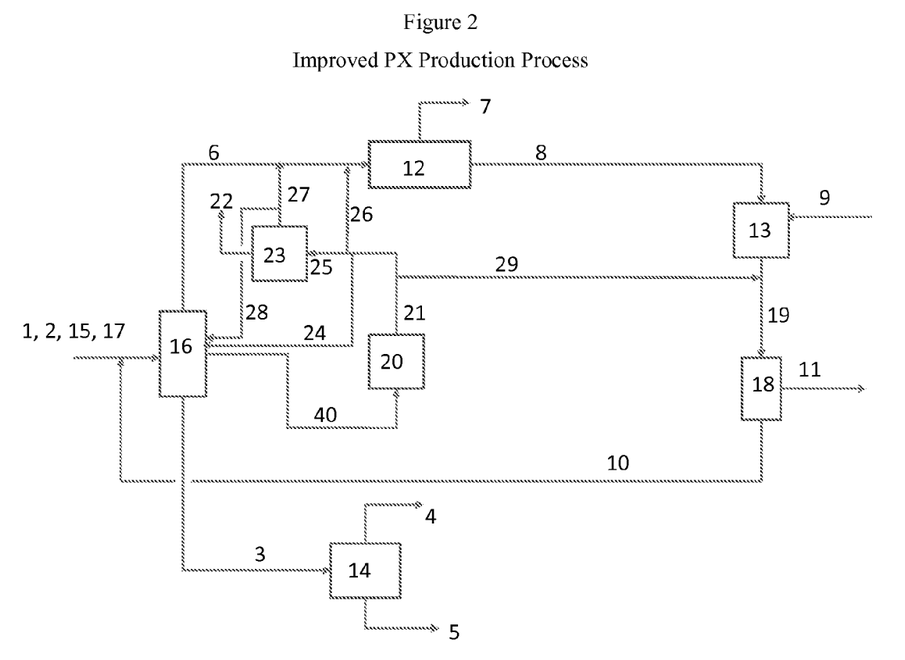
FIG. 2 is a schematic illustrating an embodiment of the invention.

The invention will be better understood by reference to FIG. 2, which illustrates a specific embodiment of the invention. It will be understood by one of skill in the art that FIG. 2 is merely representative of the present invention and that many variations thereof can be readily envisioned. Moreover, various valves, heating and cooling devices, compressors, and the like are not shown for convenience of view but would also be readily apparent to one of skill in the art.

As shown in FIG. 2, various feed sources comprising $C_8^+$ aromatics, such as 1, 2, 15, and 17, as identified above, are sent to fractionator 16, which removes $C_9^+$-aromatics and, optionally, OX from the feed. The $C_8$-aromatics overhead is sent via line 6 to PX recovery 12, which may be provided by a crystallization unit or selective adsorption unit (such as a Parex™ unit) both of which are known in the art. PX is taken off in line 7 and the PX-depleted stream 8 comprising a majority of $C_8$ aromatics other than PX is sent to vapor-phase xylenes isomerization 13, having a source of hydrogen 9 to generate a first isomerate (or isomerization product) stream 19 having a near-equilibrium concentration of xylene isomers. The isomerate stream 19 passes to detoluenization fractionation 18 which removes $C_7^-$ hydrocarbons in stream 11 to yield isomerate recycle stream 10 which is processed in fractionator 16.

Continuing with the description of FIG. 2, a PX liquid stream 40 having a lower PX concentration than said $C_8$-aromatics overhead is drawn from fractionator 16 at locations where the number of the drawing tray is in between 30% to 80% of the total tray number (counting from the top to the bottom of the fractionator). Stream 40 is sent to liquid-phase isomerization unit 20 to generate a second isomerate stream 21 having a near-equilibrium concentration of xylene isomers. Stream 21 may be recycled via line 24 to fractionator 16 at the same drawing tray or at above the drawing tray for stream 40 to assist the separation in fractionator 16 with the increased PX concentration. Optionally, the bottoms product 3 from fractionator 16 may be advantageously fractionated in 14 to yield an overheads product 4 of OX and bottoms product 5 of $C_9^+$-aromatic hydrocarbons.

FIG. 2 also shows that the liquid-phase isomerate stream 21 may be optionally sent to one or more locations such as to fractionator 16 via line 24, to benzene removal 23 via line 25, to detoluenization fractionation 18 via line 29, and directly to PX recovery 12 via line 26. The amount sent to each location is determined by the need to remove by-products which include benzene, and $C_9^+$-aromatics. The by-products from liquid-phase xylenes isomerization 20 in the liquid-phase isomerate stream 21 may need to be adjusted (typically down) to a level that is acceptable for PX recovery 12 especially if selective adsorption is used for recovering PX. The $C_9^+$-aromatics can be removed in fractionator 16 or in one or more devices that employ separation techniques such as membrane, extraction, and adsorption. Similarly, benzene can be removed in 23 to generate a benzene-rich stream 22 and a benzene depleted stream 27 using one or more devices that employ separation techniques such as distillation, extraction, membrane, and adsorption. Optionally, at least a portion of the benzene-depleted stream can be sent to PX recovery 12 via line 27 and/or fractionator 16 via line 28. Optionally, the $C_9^+$-aromatics and benzene can be removed simultaneously using one or more devices that employ separation techniques such as distillation, extraction, membrane, and adsorption.

Figure 3:
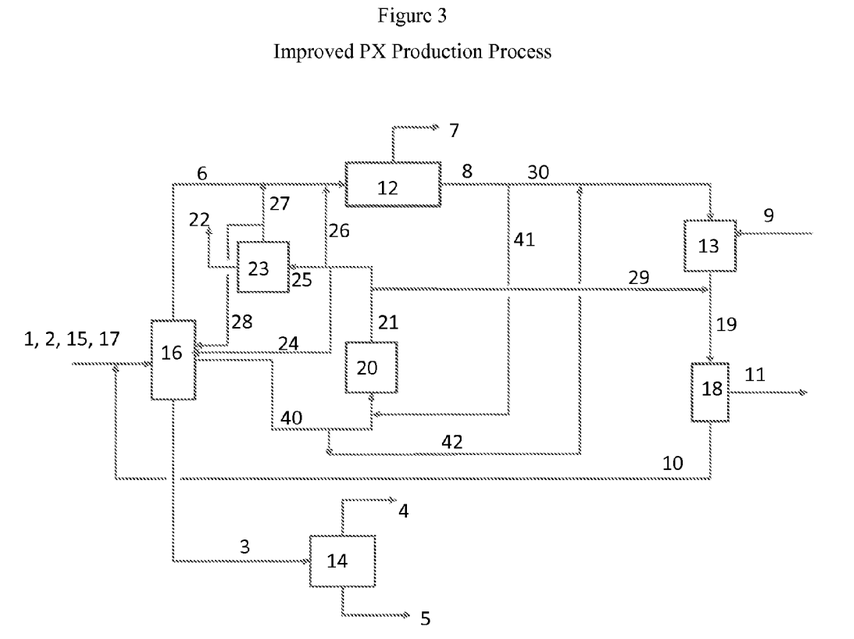
FIG. 3 is a schematic illustrating several additional embodiments of the invention.

FIG. 3 shows another embodiment of the invention. It will be understood by one of skill in the art that FIG. 3 is merely representative of the present invention and that many variations thereof can be readily envisioned. Moreover, various valves, heating and cooling devices, compressors, and the like are not shown for convenience of view but would also be readily apparent to one of skill in the art.

As shown in FIG. 3, various feed sources comprising $C_8^+$ aromatics, such as 1, 2, 15, and 17, as identified above, are sent to fractionator 16, which removes $C_9^+$-aromatics and, optionally, OX from the feed. The $C_8$ aromatics overhead is sent via line 6 to PX recovery 12, which may be provided by a crystallization unit or selective adsorption unit both of which are known in the art (such as a Parex™ unit). PX is taken off in line 7 and the PX-depleted stream 8 comprising other non-PX $C_8$ aromatics is split and sent in parallel to vapor-phase xylenes isomerization 13, having a source of hydrogen 9, and liquid-phase xylenes isomerization 20 via lines 30 and 41, respectively. The isomerate 19 passes to detoluenization fractionation 18 which removes $C_7^-$ hydrocarbons in stream 11 to yield isomerate recycle stream 10. Isomerate recycle stream 10 is processed in fractionator 16.

WO 2012/058106 and WO 2012/058108 have shown that splitting the PX-depleted stream 8 into streams 30 and 41 can significantly reduce energy consumption by moving streams away from the vapor phase xylene isomerization 13, which is more energy intensive than liquid-phase isomerization 20, and controlling the amount of $C_9^+$-aromatics that are processed in fractionator 16. Isomerate recycle 10 from vapor phase xylenes isomerization 13 is decreased by this process scheme and the amount of $C_9^+$-aromatics that are processed in fractionator 16 is better controlled.

This invention unexpectedly discovered that more energy savings and/or capacity increases can be achieved by drawing a PX-lean liquid stream 40 from fractionator 16 at locations where number of the drawing tray is in between 30% to 80% of the total tray number (counting from the top to the bottom of the fractionator). Stream 40 and stream 41 are sent to liquid-phase isomerization unit 20 to generate a second isomerate 21 having near-equilibrium xylenes concentration, which may be recycled back to fractionator 16 at the same drawing tray or at above the drawing tray for stream 40 to assist the separation in fractionator 16 with the increased PX concentration. Because stream 40 may contain relatively higher concentration of $C_9^+$-aromatics, if controlling the amount of $C_9^+$-aromatics passing through liquid-phase isomerization unit 20 is desirable, optionally at least a portion of stream 40 may be sent via line 42 to the vapor-phase isomerization unit 13, which may accommodate more $C_9^+$-aromatics. The amount sent via lines 30, 41, and 42 will be determined by balancing energy savings and control of $C_9^+$-aromatics. Optionally, the bottoms product 3 from fractionator 16 may be advantageously fractionated in 14 to yield an overheads product 4 of OX and bottoms product 5 of $C_9^+$-aromatic hydrocarbons.

FIG. 3 also shows that liquid-phase isomerate recycle stream 21 can be optionally sent to one or more locations such as to fractionator 16 via line 24, to benzene removal 23 via line 25, to detoluenization fractionation 18 via line 29, and directly to PX recovery 12 via line 26. The amount sent to each location is determined by the need to remove by-products which include benzene, and $C_9^+$-aromatics. The by-products from liquid-phase xylenes isomerization 20 in the liquid-phase isomerate stream M may need to be adjusted down to a level that is acceptable for PX recovery 12 especially if selective adsorption is used for recovering PX. The $C_9^+$-aromatics can be removed in fractionator 16 or in one or more devices that employ separation techniques such as membrane, extraction, and adsorption. Similarly, benzene can be removed in 23 to generate a benzene-rich stream 22 and a benzene-depleted stream 27 using one or more devices that employ separation techniques such as distillation, extraction, membrane, and adsorption. Optionally, at least a portion of the benzene-depleted stream can be sent to PX recovery 12 via line 27 and/or fractionator 16 via line 28. Optionally, the $C_9^+$-aromatics and benzene can be removed simultaneously using one or more devices that employ separation techniques such as distillation, extraction, membrane, and adsorption.

While the embodiments disclosed in FIGS. 2 and 3 describe a separate liquid-phase isomerization unit 20 connected to $C_9^+$-aromatics fractionator 16 via middle stream 40 and recycle stream 24 and/or recycle stream 28, it will be understood by one of ordinary skill in the art that FIGS. 2 and 3 are merely representative of the present invention and that many variations thereof can be readily envisioned. For example, it is realized that the liquid-phase isomerization unit can be incorporated into the fractionator in the form of catalytic distillation or reactive distillation in which the isomerization catalyst is installed inside the fractionation column as packing to effect the desired separation and isomerization within one equipment, simultaneously. In this regard, see for example, WO 99/38823 in which a process for xylenes production by reactive distillation is disclosed.

Regarding separation of xylenes in the PX recovery, two preferred methods are fractional crystallization and selective adsorption, the details of which are known in the art. See, for instance, in this regard, U.S. Pat. No. 7,439,412, and also references cited in the Background section above.

Likewise, the details of vapor-phase xylenes isomerization and liquid-phase xylenes isomerization are also known in the art. In this regard, see for example, U.S. Pat. Nos. 6,180,550; 6,448,459; 6,872,866; 7,244,409; 7,371,913; 7,495,137; 7,592,499; 8,273,934; U.S. application Ser. No. 12/612,007, and WO 2011/133326.

Similarly, the details of the fractionator for separating $C_9^+$-aromatics and $C_8$ aromatics are known in the art. In this regard, see for example, U.S. Patent Application Publication No. 2009/0139852 in which an apparatus of dividing-wall column for the separation of a feed by distillation into a low boiler, a medium boiler, and a high boiler was disclosed.

This invention also relates to:

1. A process for producing para-xylene, PX, the process comprising:
   (a) supplying at least one hydrocarbon feed comprising $C_8^+$ aromatics to a PX production system comprising a $C_9^+$-aromatics-removal system, a PX-recovery system, a first isomerization system, a second isomerization system, and a $C_7^-$ hydrocarbons-removal system;
   (b) separating $C_9^+$-aromatics from said feed in said $C_9^+$-aromatics-removal system to recover at least one $C_8$-aromatics stream, at least one PX-lean stream having a lower PX concentration than said $C_8$-aromatics stream, and at least one $C_9^+$-aromatics-rich stream;
   (c) separating said $C_8$-aromatics stream in said PX-recovery system to recover a PX-rich stream and a PX-depleted stream;
   (d) isomerizing at least partially in the vapor phase said PX-depleted stream in said first isomerization system to produce a first isomerized stream having a higher PX concentration than said PX-depleted stream;
   (e) separating C7− hydrocarbons from said first isomerized stream in said C7− hydrocarbons-removal system to produce a C7− hydrocarbons-rich stream and a C7− hydrocarbons-depleted isomerized stream having a lower C7− hydrocarbons concentration than said first isomerized stream;
   (f) recycling said $C_7^-$ hydrocarbons-depleted isomerized stream to said $C_9^+$-aromatics-removal system;
   (g) isomerizing, at least partially, in the liquid phase said PX-lean stream in said second isomerization system to produce a second isomerized stream having a higher PX concentration than said PX-lean stream; and
   (h) recycling said second isomerized stream to said $C_9^+$-aromatics-removal system.

2. The process of paragraph 1 further comprising isomerizing at least partially in the liquid phase at least a portion of said PX-depleted stream in said second isomerization system to produce at least a portion of said second isomerized stream having a higher PX concentration than said PX-depleted stream.

3. The process of paragraphs 1 or 2 further comprising reacting at least partially in the vapor phase at least a portion of said PX-lean stream in said first isomerization system to produce at least a portion of said first isomerized stream having a higher PX concentration than said PX-lean stream.

4. The process of any of paragraphs 1 to 3 further comprising separating $C_7^-$ hydrocarbons from at least a portion of said second isomerized stream in said $C_7^-$ hydrocarbons-removal system to generate at least a portion of said $C_7^-$ hydrocarbons-depleted isomerized stream having a lower $C_7^-$ hydrocarbons concentration than said second isomerized stream.

5. The process of any of paragraphs 1 to 4 further comprising sending at least a portion of said second isomerized stream to said PX-recovery system.

6. The process of any of paragraphs 1 to 5 further comprising separating benzene from at least a portion of said second isomerized stream in a benzene removal system to produce a benzene-rich stream and a benzene-depleted stream.

7. The process of paragraph 6 and further comprising sending at least a portion of said benzene-depleted stream to said PX-recovery system.

8. The process of paragraphs 6 or 7 and further comprising sending at least a portion of said benzene-depleted stream to said $C_9^+$-aromatics-removal system.
9. The process of any of paragraphs 1 to 8, wherein said $C_9^+$-aromatics-removal system comprises at least one distillation unit.
10. The process of paragraph 9, wherein the $C_9^+$-aromatics-removal system produces an overhead stream comprising a $C_8$-aromatics stream and a bottoms stream comprising a $C_9^+$-aromatics-rich stream.
11. The process of paragraphs 9 or 10, wherein said PX-lean stream comprises, at least partially, the liquid drawn from a drawing tray of which the tray number is in between 30% to 80% of the total tray number of said distillation unit(s).
12. The process of paragraph 11, wherein at least a portion of said second isomerized stream and/or benzene-depleted stream is recycled to said $C_9^+$-aromatics-removal system at the same location as the drawing tray.
13. The process of paragraph 11 or 12, wherein at least a portion of said second isomerized stream and/or benzene-depleted stream is recycled to said $C_9^+$-aromatics-removal system at a tray located above said drawing tray.
14. The process of any of paragraphs 9 to 13, wherein said distillation unit comprises at least one dividing-wall distillation unit.
15. The process of any of paragraphs 9 to 14, wherein at least a portion of said second isomerization system is installed inside said distillation unit in the form of catalytic distillation to effect said isomerization and said separation.
16. The process of any of the preceding paragraphs, wherein said $C_7^-$ hydrocarbons-removal system comprises at least one distillation unit.
17. The process of any of the preceding paragraphs, wherein said PX recovery system comprises a fractional crystallization unit and/or a selective adsorption unit for recovering said PX-rich stream.
18. The process of any of the preceding paragraphs, wherein each of said isomerizations comprise at least one of xylenes isomerization, ethylbenzene dealkylation, and ethylbenzene isomerization.
19. The process of any of the preceding paragraphs further including separating said $C_9^+$-aromatics-rich stream in an ortho-xylene-recovery system to produce an ortho-xylene-rich stream and an ortho-xylene-depleted $C_9^+$-aromatics stream.
20. The process of any of the preceding paragraphs, wherein the PX concentration among the xylenes in said $C_8$-aromatics stream is above the PX equilibrium concentration.
21. The process of any of the preceding paragraphs, wherein said feed comprising $C_8^+$ aromatics includes at least one feed selected from the group consisting of a $C_8^+$ selective toluene disproportionation product, a $C_8^+$ transalkylation product, a $C_8^+$ reformate product, a $C_8^+$ toluene disproportionation product, and a $C_8^+$ toluene methylation product, and a $C_8^+$ benzene methylation product.
22. An apparatus for the production of para-xylene, PX, and, optionally, ortho-xylene, OX, comprising a first fractionation column operating at conditions suitable for the separation of $C_8^+$ aromatics streams into: a) a $C_8$-aromatics overhead stream; b) a PX-lean middle stream having a lower PX concentration than said $C_8$-aromatics overhead stream; and c) a $C_9^+$-aromatics-rich bottom stream, where said $C_8$-aromatics overhead stream is fluidly connected with a PX-recovery unit, wherein said PX-recovery unit provides a PX-rich stream and a PX-depleted stream, where said PX-depleted stream is fluidly connected with a vapor-phase isomerization unit to produce a first isomerized stream which is fluidly connected with a second fractionation column operating at conditions suitable for separating said first isomerized stream into a $C_7^-$ hydrocarbons-rich overhead stream and a $C_7^-$ hydrocarbons-depleted bottom stream, where said $C_7^-$ hydrocarbons-depleted bottom stream is fluidly connected with said first fractionation column to effect a recycle, where said PX-lean middle stream is fluidly connected with a liquid-phase isomerization unit to produce a second isomerized stream which is connected fluidly with said first fractionation column to effect another recycle.
23. The apparatus of paragraph 22 and further comprising connecting fluidly said PX-depleted stream with said liquid-phase isomerization unit so that a portion of said PX-depleted stream is passed to said liquid-phase isomerization unit and another portion of said PX-depleted stream is passed to said vapor-phase isomerization unit.
24. The apparatus of paragraph 22 or 23 and further comprising connecting fluidly said PX-lean middle stream with said vapor-phase isomerization unit so that a portion of said PX-lean stream is passed to said vapor-phase isomerization unit and another portion of said PX-lean stream is passed to said liquid-phase isomerization unit.
25. The apparatus of any of paragraphs 22 to 24 and further comprising connecting fluidly said second isomerized stream to said second fractionation column so that at least a portion of said second isomerized stream is passed to said second fractionation column.
26. The apparatus of any of paragraphs 22 to 25 and further comprising connecting fluidly said second isomerized stream to said PX-recovery unit so that at least a portion of said second isomerized stream is passed to said PX-recovery unit.
27. The apparatus of any of paragraphs 22 to 26 and further comprising connecting fluidly said second isomerized stream with at least one other fractionator, wherein said at least one other fractionator operates under conditions suitable for producing a benzene-rich overhead stream and a benzene-depleted bottom stream.
28. The apparatus of paragraph 27 further comprising connecting fluidly said benzene-depleted bottom stream with said first fractionation column so that at least a portion of said benzene-depleted bottom stream is passed to said first fractionation column.
29. The apparatus of paragraphs 27 or 28 further comprising connecting fluidly said benzene-depleted stream with said PX-recovery unit so that at least a portion of said benzene-depleted stream is passed to said PX-recovery unit.
30. The apparatus of any of paragraphs 22 to 29, wherein said PX-recovery unit is selected from at least one of a crystallizer and an adsorptive separator.
31. The apparatus of any one of paragraphs 22 to 30, wherein each of said isomerization units is selected from at least one of xylenes isomerization, ethylbenzene dealkylation, and ethylbenzene isomerization.
32. The apparatus of any of paragraphs 22 to 31, further including at least one separation unit downstream of said first fractionation column fluidly connected to said $C_9^+$-aromatics-rich bottom stream, whereby OX is separated from $C_9^+$-aromatics, said at least one separation unit selected from a crystallizer, a membrane unit, or a fractionation column.

EXAMPLES

Computer simulations using the PROII™ program, commercially available, were conducted to verify the benefits of the present invention. Certain assumptions were made, within the skills of the ordinary artisans in possession of the present disclosure, specifically (a) the isomerization unit isomerizes PX, MX, and OX to their thermodynamic equilibrium; (b) the equilibrium PX concentration in xylenes (excluding EB) is 24%; and (c) the isomerization unit converts EB to benzene, toluene, xylenes, or other hydrocarbons. Examples 1 to 3 illustrate the simulation results on two process arrangements: Example 1 on the conventional, state-of-the-art PX production process shown in FIG. 1, and Examples 2 and 3 on the improved process shown in FIG. 2.

Example 1

Example 1 simulates the production of PX in a typical PX plant as shown in FIG. 1 using the PROII simulation program. The results are shown in Table 1 for the $C_9^+$-aromatics fractionator 16 and Table 2 for the PX recovery unit 12, which in this study is a PAREX™ selective adsorption unit. In this simulation, fractionator 16 has 3 feed streams. Feeds 1 and 2 are fresh feeds, typically produced by a reformer. Feed 3 is the recycle stream 10 from vapor-phase isomerization unit 13 and detoluenization column 18. In the simulation, fractionator 16 produces 4.18 units of $C_8$-aromatics overhead product 6 having a PX concentration of 22.14 wt % (or 23.39 wt % on xylenes only). The simulation further assumes that the plant is limited by the rates of the PAREX raffinate, which in this simulation is 3.14 units/hr. Such a limitation is commonly encountered in commercial plants. As a result, only 4.02 units/hr of the 4.18 units/hr overhead stream was fed to the PAREX™ unit. The excess 0.16 units/hr of the overhead stream would have to be disposed of as a lower value product. Table 2 shows that the Parex™ Unit produces 0.87 units/hr of PX at 99.88 wt % purity and 3.14 units/hr of raffinate of mainly MX and OX. The PAREX also produces a small quantity of light products.

Example 2

This example illustrates the benefits of the improved process as shown in FIG. 2 using the PROII simulation at the condition of constant PX production. The simulation shows that a PX-lean liquid stream 40 at the location of Tray No. 40 in fractionator 16 can be drawn and directed to liquid-phase isomerization reactor 20 at 240° C. and 280 psig. The reactor conducts xylenes isomerization to produce more PX. In this example, it was assumed that the equilibration had an efficiency of 95% (i.e., reaching 95% of the equilibrium concentration). In this study, isomerization product 21 is returned to fractionator 16 at the same tray (i.e., Tray No. 40). The performances of fractionator 16 and the isomerization reactor 20 are presented in Table 3 and the performance of PAREX™ Unit 12 in Table 4. It is seen that the coupling of isomerization 20 and fractionation 16 raises the PX concentration in the overhead stream from the base case of 22.14 wt % to 23.29 wt % (or 23.39 wt % to 24.68 wt % on xylenes only), which is above the PX equilibrium concentration. The PX production is the same as Example 1 base case's 0.87 units/hr at 99.88% PX purity. However, the higher PX concentration reduces the PAREX raffinate rate from 3.14 units/hr to 2.95 units/hr, which in turn reduces the rate of the recycle stream to the xylenes column. Such a rate reduction would lead to an energy saving of about 5 Mega Watts for a typical PX plant.

Example 3

This example illustrates the benefits of the improved process as shown in FIG. 2 using the PROII™ simulation at the condition of plus PX production. Other conditions are unchanged from Example 2. As shown in Example 2, the proposed technology reduces the PAREX™ raffinate rate from 3.14 units/hr to 2.95 units/hr. The reduction generates an excess capacity. Plus, PX production can be accomplished by increasing the feed rate to fill up the excess capacity. The results are shown in Tables 5 and 6. It is seen that the improved process allows 4.08 units/hr of the overhead stream to be fed to the PAREX™ unit compared to the rate of 4.02 units in Example 1. Consequently, the PX production is increased from 0.87 units/hr units to 0.93 units/hr, representing a 7% capacity increase.

TABLE 1

Example 1 Base Case: Performance of Fractionator 16

|  | Feed 1 | Feed 2 | Feed 3 | Bottom | Overhead |
|---|---|---|---|---|---|
| Relative Rates, unit/hr | 1.29 | 1 | 2.97 | 1.08 | 4.18 |
| Composition, wt % | | | | | |
| Benzene | 0.00 | 0.00 | 0.00 | 0.00 | 0.00 |
| Toluene | 0.03 | 0.14 | 0.30 | 0.00 | 0.26 |
| EB | 10.64 | 1.82 | 1.80 | 0.00 | 5.00 |
| PX | 10.54 | 10.46 | 23.07 | 0.00 | 22.14 |
| MX | 22.96 | 23.24 | 51.10 | 0.00 | 48.93 |
| OX | 15.23 | 10.88 | 22.93 | 0.07 | 23.57 |
| C9s | 31.72 | 39.11 | 0.63 | 75.78 | 0.04 |
| C10+ | 8.83 | 14.35 | 0.11 | 24.15 | 0.00 |
| Non-aromatics | 0.06 | 0.00 | 0.06 | 0.00 | 0.06 |

TABLE 2

Example 1 Base Case: Performance of PX Recovery Unit (PAREX) 12

|  | Feed | Extract | Raffinate | Light Products |
|---|---|---|---|---|
| Relative Rates, Unit/hr | 4.02 | 0.87 | 3.14 | 0.01 |
| Composition, wt % | | | | |
| Benzene | 0.00 | 0.00 | 0.00 | 0.00 |
| Toluene | 0.26 | 0.01 | 0.14 | 89.99 |
| EB | 5.00 | 0.01 | 6.38 | 0.00 |
| PX | 22.14 | 99.88 | 0.77 | 10.00 |
| MX | 48.93 | 0.04 | 62.49 | 0.00 |
| OX | 23.57 | 0.02 | 30.10 | 0.00 |
| C9s | 0.04 | 0.03 | 0.03 | 0.00 |
| C10+ | 0.00 | 0.01 | 0.01 | 0.00 |
| Non-aromatics | 0.06 | 0.00 | 0.08 | 0.01 |

TABLE 3

Example 2 Improved Process at Constant PX Production: Performance of Fractionator 16 and Liquid-Phase Isomerization Unit 20

|  | Feed 1 | Feed 2 | Feed 3 | 16 Bottom | 16 Overhead | Feed to 20 (Stream 40) | Products from 20 (Stream 21) |
|---|---|---|---|---|---|---|---|
| Relative Rates, Unit/hr | 1.29 | 1.00 | 2.77 | 1.08 | 3.98 | 2.81 | 2.81 |
| Composition, wt % | | | | | | | |
| Benzene | 0.00 | 0.00 | 0.00 | 0.00 | 0.04 | 0.01 | 0.06 |
| Toluene | 0.03 | 0.14 | 0.30 | 0.00 | 0.29 | 0.04 | 0.09 |
| EB | 10.64 | 1.82 | 1.90 | 0.00 | 5.19 | 6.92 | 6.87 |
| PX | 10.54 | 10.46 | 23.04 | 0.00 | 23.29 | 18.62 | 20.33 |
| MX | 22.95 | 23.24 | 50.43 | 0.00 | 51.86 | 44.47 | 49.39 |
| OX | 15.23 | 10.88 | 23.52 | 0.05 | 19.23 | 26.49 | 19.67 |

TABLE 3-continued

Example 2 Improved Process at Constant PX Production: Performance of Fractionator 16 and Liquid-Phase Isomerization Unit 20

|  | Feed 1 | Feed 2 | Feed 3 | 16 Bottom | 16 Over-head | Feed to 20 (Stream 40) | Products from 20 (Stream 21) |
|---|---|---|---|---|---|---|---|
| C9s | 31.72 | 39.11 | 0.63 | 75.57 | 0.04 | 3.34 | 3.36 |
| C10+ | 8.83 | 14.35 | 0.11 | 24.38 | 0.00 | 0.10 | 0.21 |
| Non-aromatics | 0.06 | 0.00 | 0.06 | 0.00 | 0.06 | 0.02 | 0.02 |

TABLE 4

Example 2 Improved Process at Constant PX Production: Performance of PX Recovery Unit (PAREX) 12

|  | Feed | Extract | Raffinate | Light Products |
|---|---|---|---|---|
| Relative Rates, Unit/hr | 3.82 | 0.87 | 2.95 | 0.01 |
| Composition, wt % |  |  |  |  |
| Benzene | 0.04 | 0.00 | 0.05 | 0.00 |
| Toluene | 0.29 | 0.01 | 0.16 | 89.99 |
| EB | 5.19 | 0.01 | 6.73 | 0.00 |
| PX | 23.29 | 99.88 | 0.82 | 10.00 |
| MX | 51.86 | 0.04 | 67.21 | 0.00 |
| OX | 19.23 | 0.02 | 24.92 | 0.00 |
| C9s | 0.04 | 0.03 | 0.03 | 0.00 |
| C10+ | 0.00 | 0.01 | 0.01 | 0.00 |
| Non-aromatics | 0.06 | 0.00 | 0.08 | 0.01 |

TABLE 5

Example 3 Improved Process at Plus PX Production: Performance of Fractionator 16 and Liquid-Phase Isomerization Unit 20

|  | Feed 1 | Feed 2 | Feed 3 | 16 Bottom | 16 Over-head | Feed to 20 (Stream 40) | Products from 20 (Stream 21) |
|---|---|---|---|---|---|---|---|
| Relative Rates, Unit/hr | 1.29 | 1.00 | 2.96 | 1.08 | 4.18 | 2.81 | 2.81 |
| Composition, wt % |  |  |  |  |  |  |  |
| Benzene | 0.00 | 0.00 | 0.00 | 0.00 | 0.03 | 0.01 | 0.06 |
| Toluene | 0.03 | 0.14 | 0.30 | 0.00 | 0.29 | 0.03 | 0.09 |
| EB | 10.63 | 1.83 | 1.82 | 0.00 | 4.98 | 6.67 | 6.61 |
| PX | 10.55 | 10.47 | 23.06 | 0.00 | 23.37 | 18.53 | 20.34 |
| MX | 22.96 | 23.24 | 50.47 | 0.00 | 51.97 | 44.26 | 49.39 |
| OX | 15.23 | 10.87 | 23.54 | 0.04 | 19.24 | 26.79 | 19.68 |
| C9s | 31.71 | 39.11 | 0.63 | 75.60 | 0.04 | 3.58 | 3.61 |
| C10+ | 8.82 | 14.35 | 0.11 | 24.36 | 0.00 | 0.10 | 0.21 |
| Non-aromatics | 0.06 | 0.00 | 0.07 | 0.00 | 0.07 | 0.02 | 0.02 |

TABLE 6

Example 3 Improved Process at Plus PX Production: Performance of PX Recovery Unit (PAREX) 12

|  | Feed | Extract | Raffinate | Light Products |
|---|---|---|---|---|
| Relative Rates, Unit/hr | 4.08 | 0.93 | 3.14 | 0.01 |
| Composition, wt % |  |  |  |  |
| Benzene | 0.03 | 0.00 | 0.05 | 0.00 |
| Toluene | 0.29 | 0.01 | 0.16 | 89.99 |

TABLE 6-continued

Example 3 Improved Process at Plus PX Production: Performance of PX Recovery Unit (PAREX) 12

|  | Feed | Extract | Raffinate | Light Products |
|---|---|---|---|---|
| EB | 4.98 | 0.01 | 6.46 | 0.00 |
| PX | 23.37 | 99.89 | 0.83 | 10.00 |
| MX | 51.97 | 0.04 | 67.42 | 0.00 |
| OX | 19.24 | 0.02 | 24.96 | 0.00 |
| C9s | 0.04 | 0.03 | 0.03 | 0.00 |
| C10+ | 0.00 | 0.01 | 0.01 | 0.00 |
| Non-aromatics | 0.07 | 0.00 | 0.08 | 0.01 |

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa, specifically the term "comprising" encompasses the terms "consisting essentially of," "is," and "consisting of" and anyplace "comprising" is used "consisting essentially of," "is," or "consisting of" may be substituted therefor.

What is claimed is:

1. A process for producing para-xylene, PX, the process comprising:
   (a) supplying at least one hydrocarbon feed comprising $C_8^+$ aromatics to a PX production system comprising a $C_9^+$-aromatics-removal system, a PX-recovery system, a first isomerization system, a second isomerization system, and a $C_7^-$ hydrocarbons-removal system;
   (b) separating $C_9^+$-aromatics from said feed in said $C_9^+$-aromatics-removal system to recover at least one $C_8$-aromatics stream, at least one PX-lean stream having a lower PX concentration than said $C_8$-aromatics stream, and at least one $C_9^+$-aromatics-rich stream;
   (c) separating said $C_8$-aromatics stream in said PX-recovery system to recover a PX-rich stream and a PX-depleted stream;
   (d) isomerizing at least partially in the vapor phase said PX-depleted stream in said first isomerization system to produce a first isomerized stream having a higher PX concentration than said PX-depleted stream;
   (e) separating $C_7^-$ hydrocarbons from said first isomerized stream in said $C_7^-$ hydrocarbons-removal system to produce a $C_7^-$ hydrocarbons-rich stream and a $C_7^-$ hydrocarbons-depleted isomerized stream having a lower $C_7^-$ hydrocarbons concentration than said first isomerized stream;
   (f) recycling said $C_7^-$ hydrocarbons-depleted isomerized stream to said $C_9^+$-aromatics-removal system;
   (g) isomerizing at least partially in the liquid phase said PX-lean stream in said second isomerization system to produce a second isomerized stream having a higher PX concentration than said PX-lean stream; and (h) recycling said second isomerized stream to said $C_9^+$-aromatics-removal system.

2. The process of claim 1 further comprising isomerizing at least partially in the liquid phase at least a portion of said PX-depleted stream in said second isomerization system to produce at least a portion of said second isomerized stream having a higher PX concentration than said PX-depleted stream.

3. The process of claim 1 further comprising reacting at least partially in the vapor phase at least a portion of said PX-lean stream in said first isomerization system to produce at least a portion of said first isomerized stream having a higher PX concentration than said PX-lean stream.

4. The process of claim 1 further comprising separating $C_7^-$ hydrocarbons from at least a portion of said second isomerized stream in said $C_7^-$ hydrocarbons-removal system to generate at least a portion of said $C_7^-$ hydrocarbons-depleted isomerized stream having a lower $C_7^-$ hydrocarbons concentration than said second isomerized stream.

5. The process of claim 1 further comprising sending at least a portion of said second isomerized stream to said PX-recovery system.

6. The process of claim 1 further comprising separating benzene from at least a portion of said second isomerized stream in a benzene removal system to produce a benzene-rich stream and a benzene-depleted stream.

7. The process of claim 6 and further comprising sending at least a portion of said benzene-depleted stream to said PX-recovery system.

8. The process of claim 6 and further comprising sending at least a portion of said benzene-depleted stream to said $C_9^+$-aromatics-removal system.

9. The process of claim 1, wherein said $C_9^+$-aromatics-removal system comprises at least one distillation unit.

10. The process of claim 9, wherein the $C_9^+$-aromatics-removal system produces an overhead stream comprising a $C_8$-aromatics stream and a bottoms stream comprising a $C_9^+$-aromatics-rich stream.

11. The process of claim 9, wherein said PX-lean stream comprises, at least partially, the liquid drawn from a drawing tray of which the tray number is in between 30% to 80% of the total tray number of said distillation unit(s).

12. The process of claim 11, wherein at least a portion of said second isomerized stream and/or benzene-depleted stream is recycled to said $C_9^+$-aromatics-removal system at the same location as the drawing tray.

13. The process of claim 11, wherein at least a portion of said second isomerized stream and/or benzene-depleted stream is recycled to said $C_9^+$-aromatics-removal system at a tray located above said drawing tray.

14. The process of claim 9, wherein said distillation unit comprises at least one dividing-wall distillation unit.

15. The process of claim 9, wherein at least a portion of said second isomerization system is installed inside said distillation unit in the form of catalytic distillation to effect said isomerization and said separation.

16. The process of claim 1, wherein said $C_7^-$ hydrocarbons-removal system comprises at least one distillation unit.

17. The process of claim 1, wherein said PX recovery system comprises a fractional crystallization unit and/or a selective adsorption unit for recovering said PX-rich stream.

18. The process of claim 1, wherein each of said isomerizations comprise at least one of xylenes isomerization, ethylbenzene dealkylation, and ethylbenzene isomerization.

19. The process of claim 1 further including separating said $C_9^+$-aromatics-rich stream in an ortho-xylene-recovery system to produce an ortho-xylene-rich stream and an ortho-xylene-depleted $C_9^+$-aromatics stream.

20. The process of claim 1, wherein the PX concentration among the xylenes in said $C_8$-aromatics stream is above the PX equilibrium concentration.

21. The process of claim 1, wherein said feed comprising $C_8^+$ aromatics includes at least one feed selected from the group consisting of a $C_8^+$ selective toluene disproportionation product, a $C_8^+$ transalkylation product, a $C_8^+$ reformate product, a $C_8^+$ toluene disproportionation product, and a $C_8^+$ toluene methylation product, and a $C_8^+$ benzene methylation product.

* * * * *